United States Patent [19]

Boehringer et al.

[11] Patent Number: 4,767,417

[45] Date of Patent: Aug. 30, 1988

[54] DRAINAGE DEVICE FOR COLLECTING LIQUIDS FROM A BODY CAVITY

[75] Inventors: John R. Boehringer, Wynnewood; John Karpowicz, Havertown; Steven T. Sutter, Blue Bell, all of Pa.

[73] Assignee: Boehringer Laboratories, Wynnewood, Pa.

[21] Appl. No.: 830,577

[22] Filed: Feb. 18, 1986

[51] Int. Cl.[4] ............................................. A61M 1/00
[52] U.S. Cl. .................................................... 604/31
[58] Field of Search ................... 248/95; 40/310, 594; 604/119, 318–321; 137/205

[56] References Cited

U.S. PATENT DOCUMENTS

| | | | |
|---|---|---|---|
| 3,363,626 | 1/1968 | Bidwell et al. | 128/276 |
| 3,363,627 | 1/1968 | Bidwell et al. | 128/276 |
| 3,517,450 | 6/1970 | Greco | 40/310 |
| 3,559,647 | 2/1971 | Bidwell et al. | 128/276 |
| 3,653,913 | 8/1972 | Kurtz et al. | 604/321 |
| 3,809,085 | 5/1974 | Bidwell et al. | 128/275 |
| 3,853,128 | 12/1974 | Kurtz et al. | 128/275 |
| 4,018,224 | 4/1977 | Kurtz et al. | 604/321 |
| 4,430,085 | 2/1984 | Ahrens | 604/321 |
| 4,439,190 | 3/1984 | Protzmann et al. | 604/319 |
| 4,443,220 | 4/1984 | Hauer et al. | 604/408 |
| 4,455,141 | 6/1984 | Todd | 604/321 |
| 4,544,370 | 10/1985 | Elliot et al. | 604/319 |

OTHER PUBLICATIONS

"Thora-Drain III Catalog Cot", Chesebrough-Ponds, Inc., Greenwich, Connecticut, 06830, 1980.
"Ohio Thoracic Drainage System", Ohio Medical Products, Madison, Wisconsin, 53707, 1983.
"Pneumo-Drain", Catalog Cot, Atrium Medical Corp. Amherst, N.H, 03031, 1983.
"Roberts 420-AC Pesto-Seal", Halkey-Roberts Corp., Paramus, New Jersey, 3/1983.
Chapter 4/Drainage Apparatus; pp. 67–97, The Pleural Space.
Sorenson Research advertisement for Drainage Device in Medical Electronic Products Magazine.
W. L. Gore and Associates Inc., brochure for Gore--Tex Membrane Products.
Emerson, brochure for Disposable Thoracic Drainage Sets.
Argyl, brochure for Chest Drainage Unit.
Chesebrough-Pond's Inc., brochure for Thora-Drain III, Chest Drainage System.
Halkey Medical, advertisement for Luer Style Syringe Check Valve.
Davol Inc., instructions for Chest Drainage Unit.
Howmedica, Inc., instructions for Pleur-Evac Chest Drainage Unit.
Ohio Medical Products, brochure for Thoracic Drainage System.
Beckton-Dickenston, brochure for Suction Collection Canister.

Primary Examiner—C. Fred Rosenbaum
Assistant Examiner—J. L. Kruter
Attorney, Agent, or Firm—Paul & Paul

[57] ABSTRACT

A suction drainage device is provided, particularly for collecting liquids and any solids that may be carried therewith from a cavity of a body. Suction draws air or other gases from a collection chamber, and liquid and entrained particles from the cavity are drawn into a collection chamber. The device also has a water manometer. A liquid seal is also provided through which is drawn air and other gases from the collection chamber. A fluid control valve-like device is provided between various portions, chambers, and conduits of the device, and preferably between the device itself and atmosphere, such control device preferably being a gas permeable, liquid impermeable membrane, but optionally comprising a baffle. A facility is provided for breaking up bubbles of air at the inlet to the water in the manometer. Sampling openings are also provided, as are visual indications in the event of an upset of the device, an optional visual indication for magnifying observation of an air leak, an atmosphere opening on multiple planes to prevent its accidental blocking, an optional connection to a pump for auto-transfusion purposes, further a double collection chamber for simultaneously handling two cavities, and a removable calibrated tape for recording and maintaining a permanent record of patient progress.

35 Claims, 7 Drawing Sheets

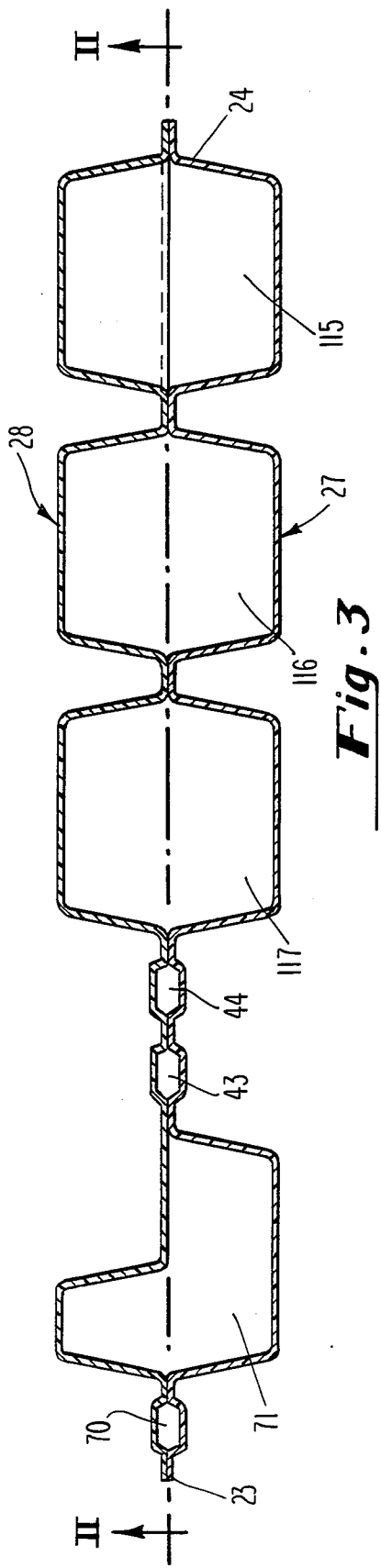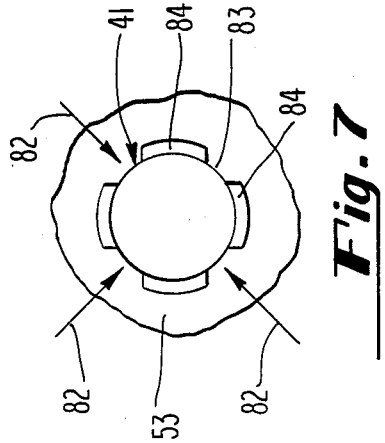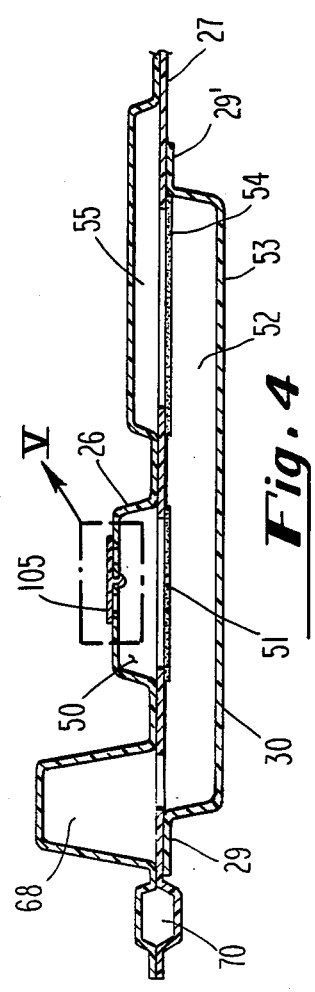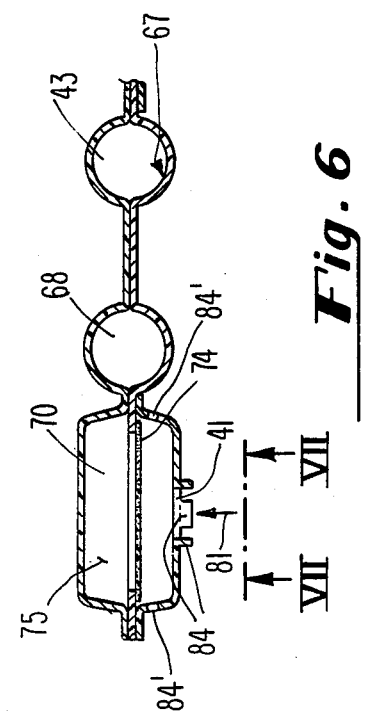

U.S. Patent    Aug. 30, 1988    Sheet 4 of 7    4,767,417
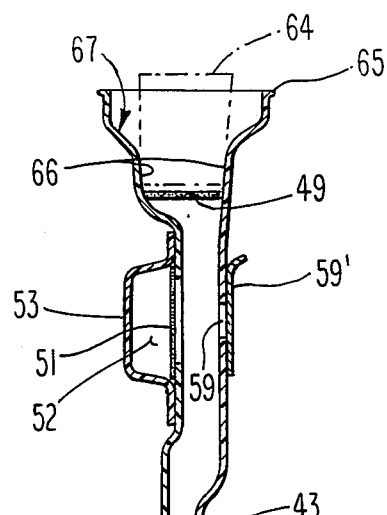
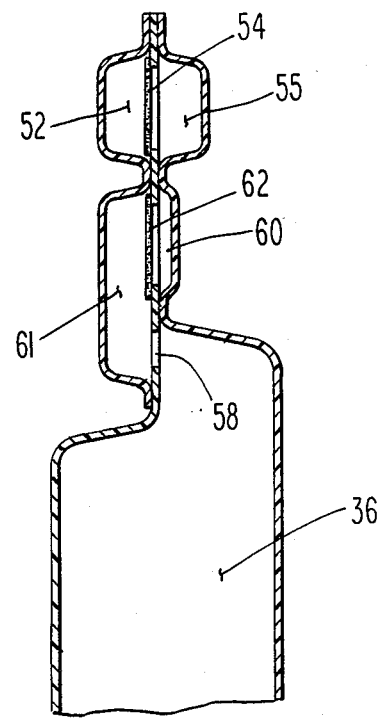
Fig. 8
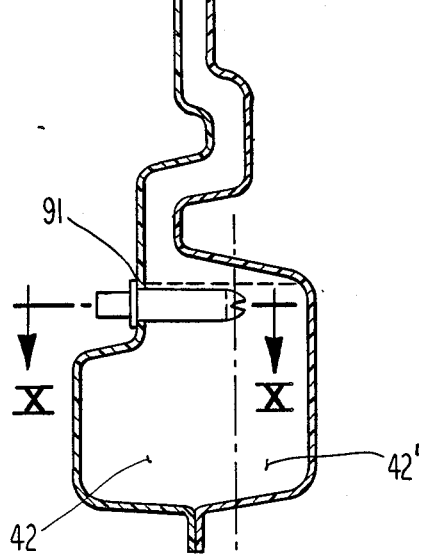
Fig. 9
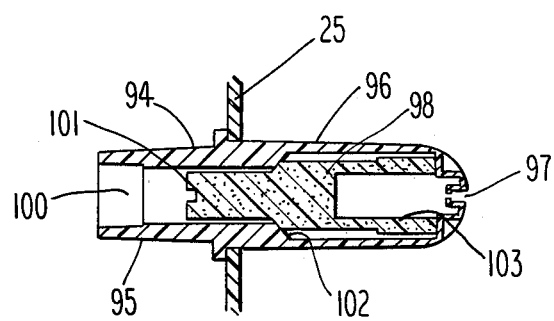
Fig. 10

DRAINAGE DEVICE FOR COLLECTING LIQUIDS FROM A BODY CAVITY

BACKGROUND OF THE INVENTION

Drainage units or devices for collecting fluids, preferably liquids and perhaps entrained solids carried therewith from body cavities, are known in the art. Initially, such devices comprised a plurality of bottles connected by hoses. One such bottle would form the collection chamber for matter being drawn from a body cavity. Another bottle formed a water seal, through which gases from the collection chamber would be bubbled, and to which the vacuum was connected. A third bottle was generally constructed as a manometer for controlling the amount of vacuum, or negative pressure of the system, to a given pressure determined by water height.

Such systems gradually developed whereby the various bottles or containers comprising the system were built into a single unit, for ease of handling in hospitals, avoidance of bottle upset, and better efficiency in general.

The present state of the art of such drainage devices remains imperfect in that they are often characterized by undesirable transfer of liquid from one of the chambers, cavities, or receptacles to another, after upset. Other disadvantages reside in susceptibility to blockage of the air inlet, ready upsetting of the devices, difficulties of filling the devices with water leading to undesirable overfill or underfill, difficulty of use by ambulatory patients, inefficient construction requiring so much room that they are readily upset, and difficulties of observation by medical personnel for determining the functioning of the vacuum, the amount of liquid being accumulated, and many other parameters.

SUMMARY OF THE INVENTION

The present invention is directed toward providing a novel drainage device or apparatus directed toward overcoming one or all of the above deficiencies in prior art devices, as well as offering additional improvements.

It is a primary object of this invention to provide a safe novel drainage device for safe evacuation collection of fluids (including gases) from a body cavity of a human being or other mammal, wherein, upon upset of the device, the loss of pressure control can be restored on reerection to normal position and undesirable intermixing of liquids within the device is prevented, vacuum seal integrity is maintained and safe shut off of vacuum and sealing of the various chambers is automatically obtained to prevent reflux to the patient.

It is a further object of this invention to provide a novel drainage device that is not readily upset.

It is another object to accomplish the above object, wherein a stand for the device may be readily packaged therewith, and rapidly assembled to give the device stability in the upstanding disposition.

It is another object of this invention to provide a novel drainage device for collection of liquids from a body cavity, in which air inlet to the device is not easily blocked.

It is a further object of this invention to provide a drainage device, in which the manometer is provided with a bubble breaker.

It is another object of this invention to provide a drainage device in which a good visual indication is provided for air leaking through the water seal.

It is another object of this invention to provide a drainage device, in which a facility is provided for separately collecting fluids simultaneously from two cavities, into two chambers separated by a liquid seal, preferably with fine resolution in each of the chambers.

Ir is another object of this invention to provide a drainage device in which sampling of liquid accumulation is provided at various stages.

It is a further object of this invention to provide a drainage device in which water may be readily added or extracted to or from the manometer and/or water seal, during use.

It is a further object of this invention to provide a drainage device that prevents liquid spillage therefrom upon upset.

It is another object of this invention to provide a drainage device that lends itself to optional auto-transfusion of blood removed from a body cavity.

It is another object of this invention to provide a permanent record of performance of the device during patient use, for later reference apart from he device.

It is a further object of this invention, to provide a visual indication of accumulation in the device of liquids removed from a body cavity, by means of a collection chamber divided into various sections, which serially fill with liquid drawn from a patient.

It is another object of this invention to provide fine resolution in a chamber; i.e., ready observation of the latest withdrawn liquid, with small liquid volume spread over a large measurable height; with the capability of emptying the fine resolution chamber as the patient's case progresses.

Other objects and advantages of the present invention will be readily understood, from a reading of the foregoing as well as the brief and detailed descriptions of the various Figures of the drawings, and other explanation of the invention as will appear hereinafter.

BRIEF DESCRIPTION OF THE DRAWING FIGURES

FIG. 3 is a cross-sectional view of the device of this invention, taken generally along the line of III—III of FIGS. 1 and 2.

FIG. 4 is a fragmentary sectional view of the upper left hand portion of the device illustrated in FIGS. 1 and 2, being taken generally along the line IV—IV of FIGS. 1 and 2.

FIG. 5 is an enlarged fragmentary sectional view of a pressure release valve shown by the designated detail V of FIG. 4, and wherein the valve is shown in full line and phantom illustration, indicating respectively, closed and opened dispositions thereof.

FIG. 6 is a fragmentary transverse view of a portion of the upper left part of the device illustrated in FIGS. 1 and 2, being taken generally along the line VI—VI of FIGS. 1 and 2.

FIG. 7 is an enlarged fragmentary elevational view of the atmosphere inlet for the device of this invention, being taken generally along the line VII—VII of FIG. 6.

FIG. 8 is an enlarged fragmentary vertical sectional view taken generally along the line VIII—VIII of FIGS. 1 and 2 of the device.

FIG. 9 is an enlarged vertical transverse sectional view, taken generally along the line of IX—IX of FIG. 2.

FIG. 10 is an enlarged sectional view, taken through the extraction valve illustrated at the lower end of FIG. 9, generally along the line of X—X of FIG. 9.

DETAILED DESCRIPTIONS OF THE PREFERRED EMBODIMENTS

Figure 1:
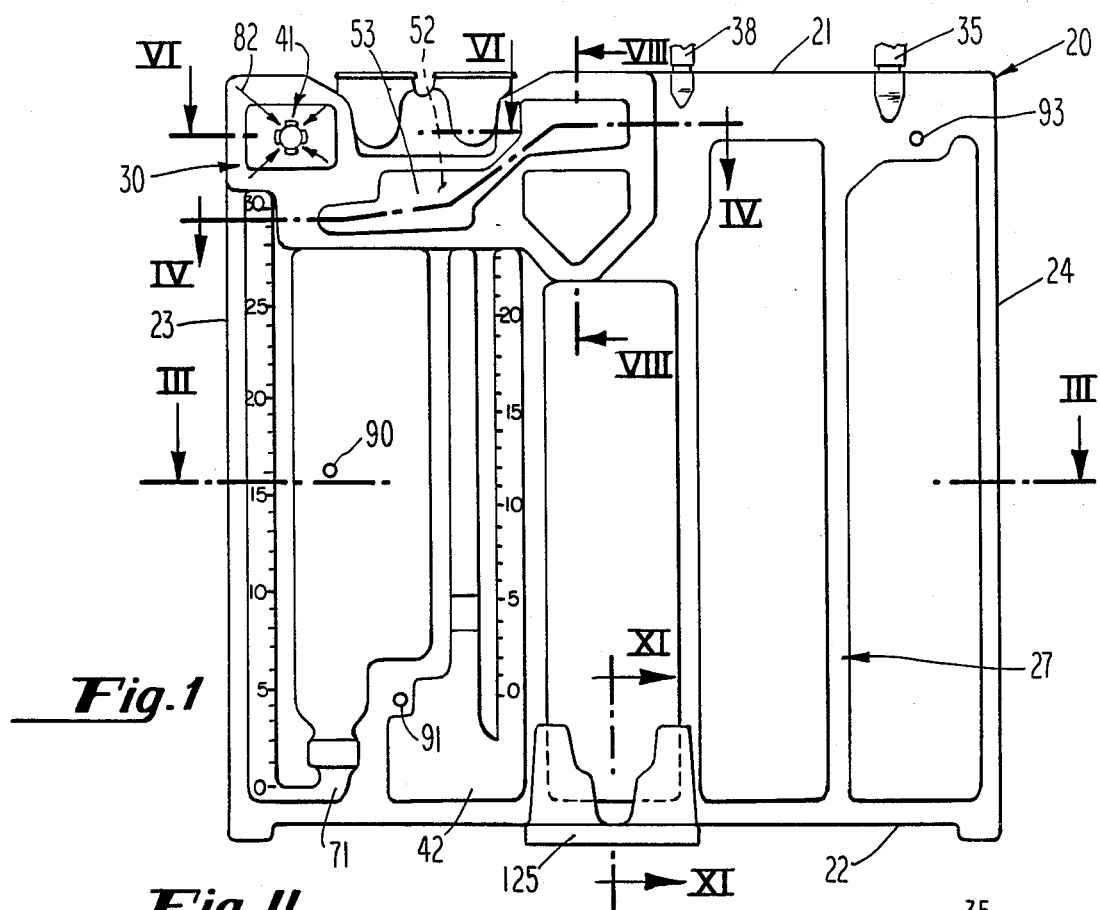
FIG. 1 is a front elevational view of the drainage device or apparatus of this invention.

Referring now to the drawings in detail, reference is first made to FIG. 1, wherein the drainage device or apparatus, preferably for use as a chest drainage unit, such as for drainage of the pleural cavity, generally designated by the numeral 20, is shown in vertical or upstanding disposition. The device 20 has upper and lower ends 21 and 22 respectively, left and right ends 23 and 24 respectively, and front and back portions 25 and 26 respectively.

While the main components of the device 20 may be constructed of various materials and formed in various ways, such as vacuum forming, injection molding or blow molding of a thermoformed plastic material or the like, in the embodiment shown the main components of the device 20 are shown to comprise front and back molded member 27 and 28, and an additional molded member 30 at the upper left corner of FIG. 1, such members being secured together along various flanges such as, but not limited to those 31, 32, 33, by means of suitable heat sealing, adhesive and/or solvent sealing techniques generally known in the art.

The device 20 is provided with a suitable hose connection as at 35, of an inlet hose from the cavity of a patient, for delivering fluids, especially liquids, possibly with a certain amount of entrained solids therein, into a collection chamber 36 of the device through an inlet opening 37. Suction to the device 20 is provided by means of a vacuum line 38, which will generally be of customary hospital supply, adjusted to 90–110 mm. Hg. of pressure, or any other suitable pressure, through vacuum opening 40. An opening to atmosphere 41 is provided, for drawing ambient air from the atmosphere into the device, as needed.

A water seal chamber 42 is provided at the lower end of the device, between generally vertically disposed conduits 43 and 44. The water level in the seal chamber 42 will generally be at the level shown by the dotted line 45 in FIG. 2, which should correspond with the level of the "0" designation shown in FIG. 1, to allow about 2 cm. of distance "D" for air or other gases to pass through, as traveling in the direction indicated by the arrow 46, along conduit 44, around the lower end 48 of separation wall 47 between the conduits 43 and 44, and up conduit 43, into conduit zone 50, through fluid control member 51 (to be described in detail hereinafter), into an interconnecting conduit 52 formed by the wall 53 of the smaller molded member 30 sealingly disposed against front wall member 25, as at flanges 29, 29′, as described above, through fluid control sheet member 54, into air/gas withdrawal zone 55 and out through the vacuum opening 40.

In passing from chamber 36 to conduit 44, air/gases pass into zone 60 which feeds to conduit 44, by first passing into zone 61 (see FIG. 8) via opening 58, and then passing through the fluid control filter membrane 62, thereby providing gas/air communication between the cavity 36 and the water seal cavity 42. It will be noted that the filter membrane 62 is constructed as a gas permeable, liquid impermeable membrane, to keep evacuate from a body cavity that has been collected in chamber 36, which will be generally in liquid form, perhaps with some solid particles therein, from entering the conduit 44 to the water seal chamber 42, but will permit gases to pass, as aforesaid.

Figure 2:
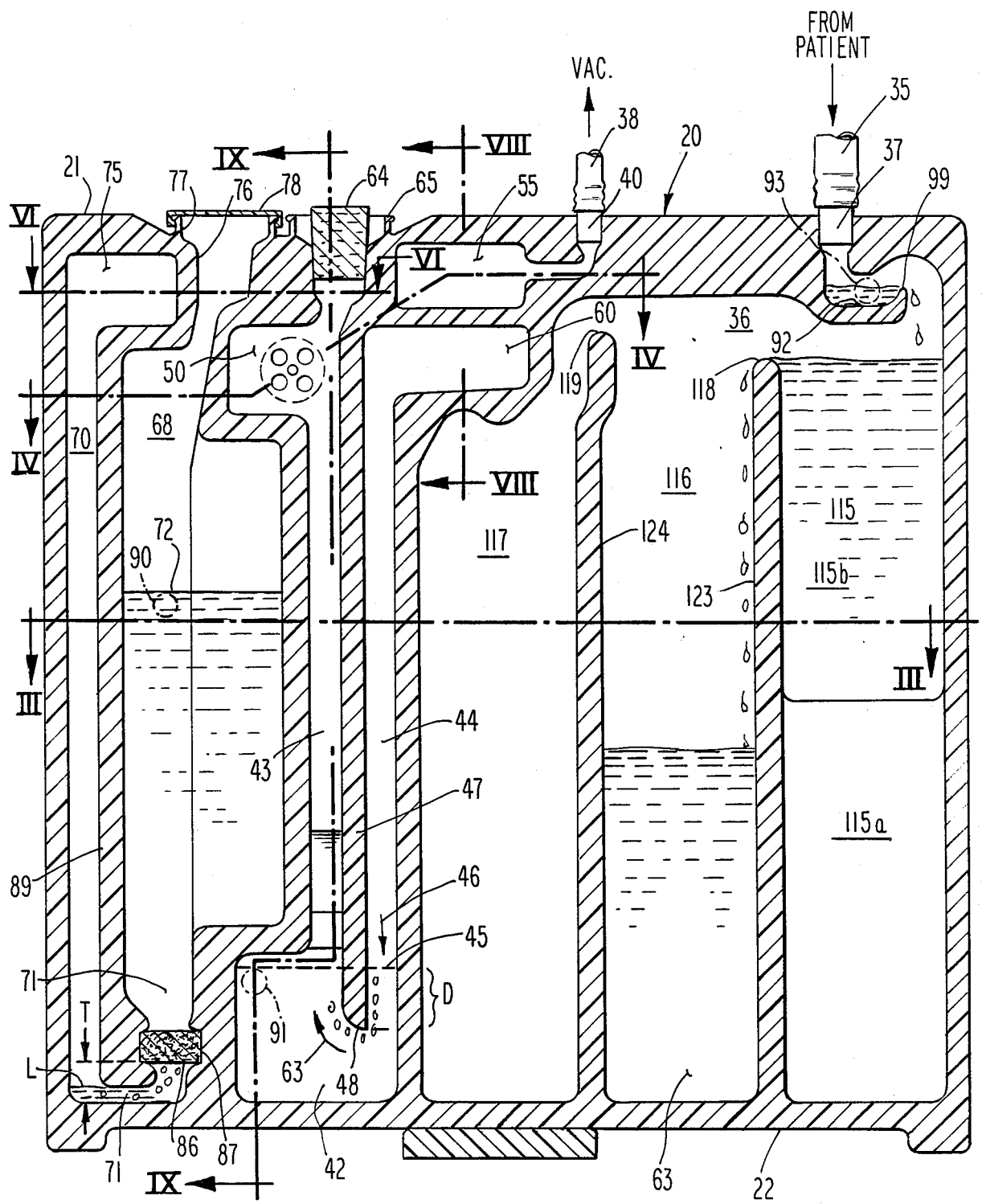
FIG. 2 is a vertical sectional view of the drainage device of this invention taken generally along the line II—II of FIG. 3.

Thus, air, including other gases, will be drawn from the chamber 36 through the water sealed cavity 42, bubbling through water contained therein, following generally the path of arrow 63 illustrated in FIG. 2, up through conduit 43, as aforesaid.

The conduit 43 has a closure 64 at its upper end, which closure may take the form of a stopper, if desired, but in the alternative, the upper end of conduit 43 is provided with a cap-receiving opening 65, for receipt of a plastic or similar snap cap thereover, in either case to prevent the passage of water from the chamber 42, outwardly of the device 20, upon upset of the device from its vertical upstanding disposition illustrated in FIG. 2. It will be noted that, with particular reference to the upper end of FIG. 9, the fill inlet 67 is generally funnel-shaped and is thus contoured, as at 66, to facilitate pouring a pre-prepared quantity of water thereinto, to form the water seal that is provided in chamber 42. The filling may be through a bacteria filter 49, in which case the water used can be non-sterile ordinary tap water.

Alternatively, filling of the water seal chamber 42 may be effected through a hole 59 in a vertical surface (FIG. 9) which hole 59 is thereafter sealed closed with a suitable tape 59′ or cap (not shown). The chamber 42 may be constructed such that when it is turned 90° onto its left side from the position illustrated in FIG. 9, a bubble of air is trapped in zone 42', limiting the amount of fill into hole 59 by an amount determined by the volume of the bubble 42', such that, when turned erect as in FIG. 9, the correct predetermined level appears in the water seal chamber. A similar air bubble trap and vertical wall fill (not shown) may also or alternatively be provided for the manometer chamber.

The vacuum draw from inlet 40, which draws through zone 55, and via interconnecting channel 52 from zone 50 as well, draws from zone 68 (see FIG. 4) in the manometer of the device 20 of this invention, which manometer essentially comprises a U-shaped structure comprising upstanding conduits 68 and 70 connected by a water chamber 71. By drawing vacuum from conduit 68, the low pressure created in that zone relative to atmospheric pressure outside the atmosphere opening 41 maintains a desired predetermined water level 72 in the manometer chamber 71, which can be visually determined relative to a predetermined desired water pressure, by reference to the numbered chart at the left end of the device illustrated in FIG. 1. Generally, a level 72 at least halfway up the chamber 71, is desired. The level of water in the manometer chamber 71 thus determines the amount of control for the suction provided by the vacuum source, to a predetermined number of inches of water pressure, such as 20 inches of water pressure, or the like.

It will be noted that, in the case of an upset, once again, gas permeable, liquid impermeable filters 51, 54, prevent water from manometer chamber 71 from entering water seal chamber 42, and the converse.

It will also be noted that, with reference to FIG. 6, another gas permeable, liquid impermeable filter membrane 74 is provided, preventing liquid from the chamber 71 that may travel up the conduit 70 and into the enlarged conduit inlet zone 75 thereof illustrated in FIG. 2, from passing outwardly through the atmosphere opening 41, but yet allowing the free passage of air through opening 41, into manometer conduit 70. It will also be noted that the upper end of conduit 68 has a funnel-like construction 76, and a cap-receiving opening 77, similar to that illustrated at the upper end of FIG. 9 for the funnel-shaped opening 67. It will further be noted that the upper end of conduit 68 is provided with a closure cap 78, as illustrated, for sealingly closing the same against discharge of water therefrom in the event of upsetting, although the cap 78 could alternately be replaced with a stopper such as that 64, or other tape or closure as desired.

Irrespective of whether a cap 78, a stopper 64, or any combination thereof is utilized, it will be noted that in either case, there is no substantial protrusion of either the fill inlets 67 and 77, or the closures 64, 78, above the plane defined by the upper end 21 of the rest of the device 20, for accommodating placement of the device 20 beneath a hospital bed, as well as for precluding unnecessary protrusions that could otherwise become engaged by hospital sheets or limbs of a patient or the like, thereby knocking the device over from an upstanding position.

The air inlet 41, open to atmosphere, is constructed for entry of air into the front wall 25 of the device, rather than through a top wall thereof, to prevent ready blockage of the same by means of a sheet or the like falling over the top 21 of the device. Additionally, air inlet through the opening 41 is provided in two planes or more, such as in a plane perpendicular to the direction of the arrow 81 illustrated in FIG. 6, as well as in the four planes that are perpendicular to the directions of the arrows 82 at the upper left corner of FIG. 1, such that air can additionally enter the slots 83 between the laterally extending protrusions 84 of the inlet 41. Alternatively, a plurality of holes 84' can be made in horizontal and vertical surfaces on the air inlet side of filter member 74 to allow air inlet in a plurality of planes.

With reference to FIG. 2, it will be noted that the manometer is provided with a bubble breaker 86 shown seated in a molded seat 87 at the lower left end thereof, disposed a predetermined distance "T" above the bottom of chamber 71 such that air bubbles entering the liquid in the manometer below the level "L" have a short distance to travel (approximately 1 cm. upwardly after passing around the lower end of manometer separation wall 89, such distance "T" being sufficient to enable the bubbles to attain enough velocity to break when they strike against the bubble breaker 86. The bubble breaker 86 is preferably constructed of a reticulated foam material of a sufficiently fine porosity that large bubbles will not pass into the liquid zone thereabove.

It will be apparent that the graduations illustrated at the left end of FIG. 1 for the manometer and for the water seal tube provide certain desirable visible indications. With respect to the manometer, the attendant can watch that the desired suction strength is provided for drawing liquid from the cavity to be drained, with rather precise measurement. Additionally, the attendant can make adjustments if need be, by adding water through the water inlet opening 77, as may be desired, to maintain the desired pressure. With respect to the water seal, the narrow column or conduit 44 that is thus graduated gives the attendant an ability to see unusual excursions of air, in the form of bubbles, coming from chamber 36, through the water seal. The level of water in the column or conduit 44 can also be observed. For example, a rise in the level of water due to a patient sucking back air from chamber 36, such as during a coughing spell, can give a visual indication for the attendant of a condition that needs attention.

A mechanism is provided for extracting water or other liquids from different locations of the device 20. For example, water can be extracted from the manometer, as for example in the case of an overfilling of the same, by withdrawing it from an access opening or port 90 of the type that is normally closed, but which may be open upon insertion of an appropriate tool, such as a needle-less syringe. Similarly, water can be added to or extracted from the water seal chamber 42 via access opening or port 91, similarly constructed. It will be noted that the water level 45 for chamber 42 is generally slightly above the location of the port 91, whereby extraction is facilitated during actual conditions of use of the device 20.

With reference to FIG. 4, the location of filter 51, so as not to be disposed across connecting conduit 52 between zones 50 and 68, is important to avoid undesirably large pressure drop there, in view of the desirably large flow from the manometer zone 68 than from the water seal zone 43, 50.

With reference to the right uppermost corner of FIG. 2, it will be seen that a trough 92 is provided just below the inlet 37 for liquid material, with the trough terminating rightward in a dam 99 for accumulating a small amount of just-removed liquid from the cavity therein.

As additional liquid is accumulated, liquid overflows the dam, into an adjacent section of the chamber 36 therebelow. It will be noted that another extraction port 93 is provided, in this case, in the vicinity of the trough 92, again for withdrawal of liquid, in this case liquid (with perhaps entrained solid particles therein) most recently drawn into the device from the body cavity.

With particular reference to FIGS. 9 and 10, reference will be made to the access means, in the form of a valve, for removing liquid from the water seal at the location of port 91, it being understood that similar valve arrangements are preferably provided for the locations of liquid access ports 90 and 93, as well. The access port 91 is provided with a commercially available valve 94, of suitable plastic construction or the like, normally solvent bonded to the wall 25 in which it is disposed. The valve is normally of two-piece construction, comprising an outer protruding tubular portion 95, and an inner protruding portion 96, with the portion 96 having a liquid access port 97 at its innermost end. A pressure-deformable member 98 is disposed therein, such that, upon insertion of a needle-less syringe into opening 100, against outer end 101 of deformable member 98, will move the deformable member 98 back off its valve seat 102, whereby liquid entering opening 97 will be able to pass through openings (not shown) in wall portions 103, past valve seat 102, and out through opening 100, into the receiving cavity of a needle-less syringe, not shown. Access ports 90 and 91 are located vertically in their chambers to provide a lower limit in each case for extracting liquid therethrough while the device is vertically disposed, to prevent withdrawing too much liquid during the extraction process. The reason for this is that a sufficient liquid level must exist to half fill the manometer and liquid seal components of the device to wet the gas permeable, liquid impermeable members when the unit is tipped 90° from the vertical of FIG. 1, so that the members will be wet so as to function as seals when the unit is upset. As an alternative to the needless syringe and valve 94, the openable ports can be of the automatically resealable type involving a rubber septum (not shown) for access via a hypodermic needle.

With respect to the gas permeable, liquid impermeable sheet members 74, 51, 54 and 62, such are preferably each of filter material, in generally vertical disposition as shown in the Figures, in the vertical or upstanding position of the device 20. Such filter members are substantially hydrophobic, and in a preferred construction may have a polypropylene scrim fabric or polyester nonwoven fabric backing. A typical such filter will be porous insofar as air or other gases are concerned, but is water or liquid-impermeable, at the pressures that will be encountered in the present device. The openings in the filters may for example be about 5 microns in the case of filters 51, 54 and 62, and 1 micron in the case of filter 74. The filter material is commercially available.

In the event of a sudden increase in pressure in chamber 36, provided from the cavity being drained, such as by coughing or the like, it may be desirable to permit a release of such pressure. To this end, there is provided a positive pressure blowout valve 105 on the back wall 26 of the device, whereby air pressure in the chamber 36 may travel, as aforesaid, via chamber 61, to chamber 60 down through conduit 44, through water chamber 42 and the seal provided therein, up through conduit 43, into zone 50 as seen in FIG. 4, and out through high pressure discharge openings 106, in the direction of arrows 107 shown in FIG. 5. The valve 105 is carried on outer wall 26, by means of a central protrusion 108 extending through a hole in wall 26, with enlarged head 110 gripping the interior of the wall 26, such that the umbrella-like portion 111 thereof will move outwardly under pressure, away from covering the holes 106, from the full line position thereof illustrated in FIG. 4, to the phantom line position thereof illustrated in FIG. 5, whereby the air or other gases may escape as indicated by the arrows 112. Alternatively, the valve 105, may be placed in a recess of outer wall 26, to prevent its accidental engagement and opening.

It will be noted that the chamber 36 as illustrated in FIG. 2 is provided with three chamber sections 115, 116, and 117. These chamber sections are free of communication except at the upper ends, over tops 118 and 119 of dividers 123 and 124 respectively. As illustrated in FIG. 2, liquid from the collection chamber inlet opening 37 has filled the trough 92, and is dripping downwardly over the dam 99 thereof into chamber section 115, in which it has filled, and liquid therefrom has spilled over the top 118 of divider or separator 123, and is now in the process of filling chamber section 116. Upon the filling of chamber section 116, there will remain the chamber section 117, to be filled, when liquid spills over the top 119 of divider or separator 124. It will be noted that for chamber 115, the lower end 115a thereof is of lesser depth from front to back of the device than the upper end 115b of chamber section 115. This allows the initial material of liquid, with perhaps entrained solids, provided from the cavity being drained, to fill the chamber section 115a more rapidly in a vertical direction, for clearer observation by the medical attendant.

Figures 11, 12, 13:
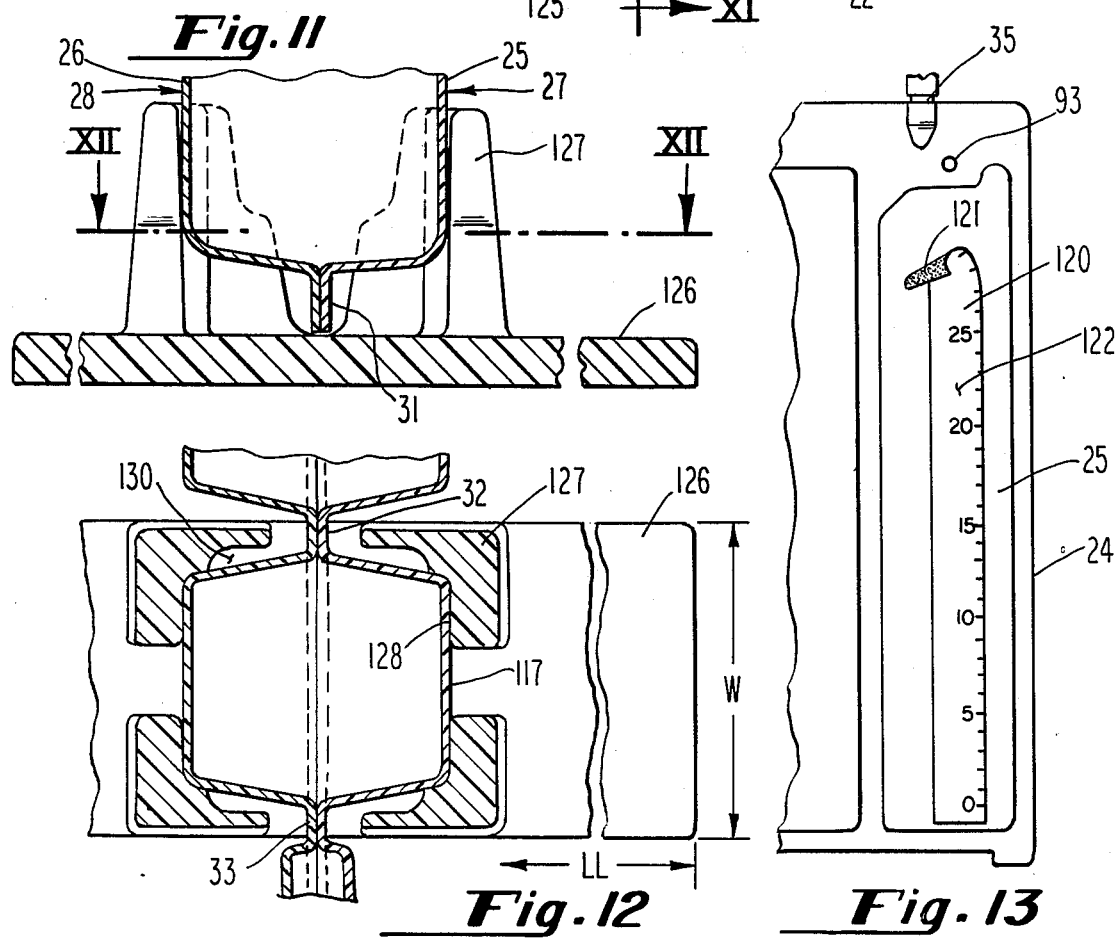
FIG. 11 is an enlarged fragmentary transverse sectional view taken through the stand and lower end of the device, generally along the line of XI—XI of FIG. 1.
FIG. 12 is a sectional view taken through the device and stand, generally along the line of XII—XII of FIG. 11.
FIG. 13 is a fragmentary elevational view of the right end of the device illustrated in FIG. 1, with a removable patient record tape shown thereon.

With respect to such observation, there is provided a removable record member 120, as is illustrated in FIG. 13. The removable record member 120 comprises a tape, generally with indicia that will correspond to measurements of volume, such as a unit measurement in cc.'s of liquid accumulated in cavity section 115. The member 120 will generally be provided in the form of a tape having a release strip behind it, for removal of the strip, and adherence of the tape to the outer wall 25 of the device 20, as illustrated in FIG. 13, by means of an adhesive backing 121 provided on the tape. The exterior surface 122 of the tape will normally be of a type that can accommodate writing thereon, such that the attendant, such as in the instance of a medical attendant to a patient, can write the patient's name on the tape, the time of each measurement, etc. This tape can form a permanent record for the patient, such that it can be removed and then adhesively secured to the patient's medical chart. In lieu of removable adhesive tape, a tape with a perforated or other tear-off means for accomplishing the same purpose may be provided. Similarly, other tapes can be provided on the front of other chamber sections 116 and 117, or even other chamber sections yet to be discussed hereinafter.

With reference to FIGS. 1, 11 and 12, in particular, it will be noted that a removal base 125 is provided for the device 20. The base 125 comprises an elongated rectangular plate 126, of substantially greater length "LL" than its width "W", as indicated in FIG. 12, such that, when it is disposed with its upstanding fingers 127 in mechanical engagement, with the exterior of a chamber section 117, either by friction fit gripping engagement as shown, or by locking therewith as by projection or male/female detent engagement (not shown), as desired, as at 128, it can hold the upstanding device, as illustrated in FIG. 1, securely supported against forward or backward falling, or tipping over. Thus, the upstanding projections 127 form a socket 130 therebetween. In use, when the device 20 is to be retained in its upstanding disposition, the base is applied as illustrated in FIGS. 1, 11 and 12. However, prior to use of the device 20, the base can be efficiently shipped with the unit, as a non-protrusive element in that it is packaged with the base rotated 90 degrees clockwise or counterclockwise as viewed in FIG. 12 relative to the chamber section 117, such that the outwardly extending legs of the base are retained below bottom 22 of the device, and are free of outward protrusions relative thereto, in front and rear directions. Similarly, after use of the device, the base can be similarly rotated for efficient storage beneath the chambers of the device.

Figure 14:
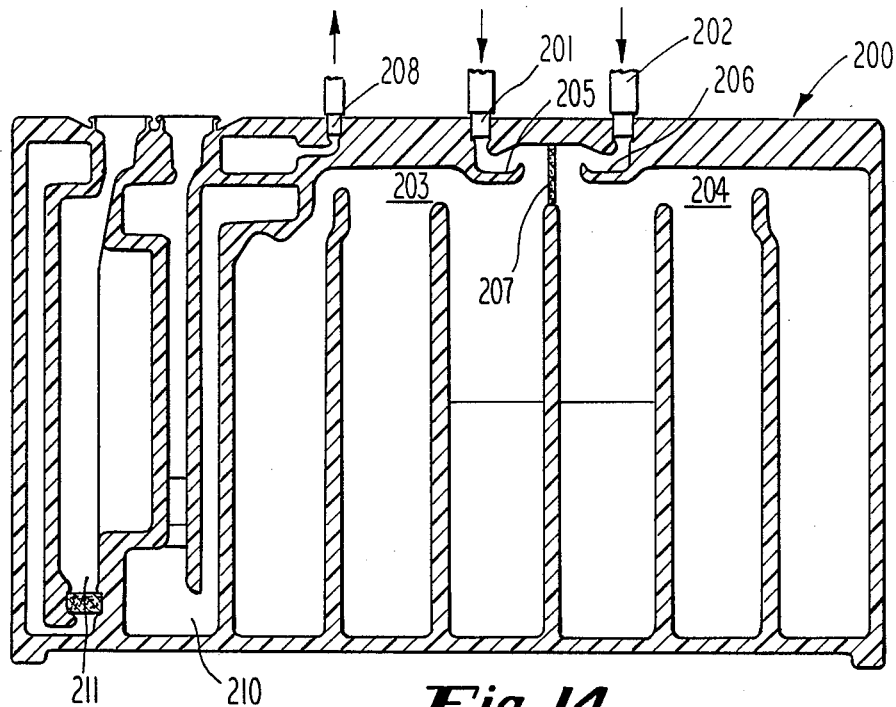
FIG. 14 is a vertical sectional view through a modified form of the device of this invention to that illustrated in FIG. 2, wherein double cavity drainage is provided.

With the reference to FIG. 14, there is shown an alternative embodiment of the present invention 200, in which a pair of liquid inlets 201 and 202 are provided, for delivery of liquid from a pair of cavities simultaneously, into a corresponding pair of collection chambers 203, 204, respectively. The chambers 203 and 204 are each provided with sampling troughs 205 and 206, and the chambers are separated from each other by a gas permeable, liquid impermeable sheet filter membrane 207, as described above, for permitting a single vacuum opening 208 to draw liquid from a pair of cavities. Each of the chambers 203, 204 are provided with multiple sections as aforesaid. Preferably, a single water sealed chamber 210 is utilized, as is a single manometer chamber 211, all as described above with respect to the preferred embodiment.

Figure 15:
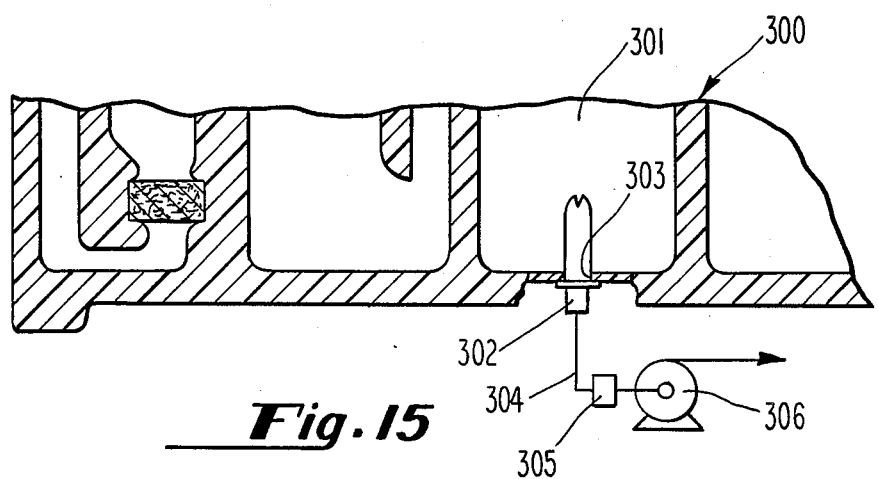
FIG. 15 is a fragmentary vertical sectional view through the lower end of a modified form of the device of this invention, wherein the device is provided with a connection for auto-transfusion.

With reference now to FIG. 15, there is illustrated another alternative embodiment for the device 20 of this invention, in which facility is provided for auto-transfusion of blood that is removed from a body cavity in accordance with the several embodiments of this invention, in which the blood is delivered into a chamber section 301 of a collection chamber of a device 300. Other structures of the device 300 may be pursuant to the embodiments otherwise described herein. However, in this embodiment, an extraction valve 302 is provided in an opening 303 preferably at a lower end of the collection device, with the valve 302 being generally constructed along the lines of that illustrated in FIG. 10. The valve in such a case is connected via feed line 304 to appropriate filter or other processing device 305, and to a blood pump 306, for re-injection into the patient. Such auto-transfusion apparatus is particularly desirable during operations in which it is not desired to use blood from another source than the patient's own body, in order to prevent disease from exterior contamination.

Figure 16:
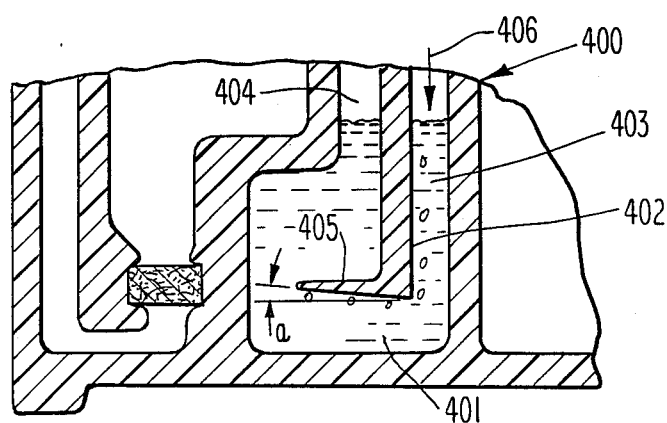
FIG. 16 is a fragmentary vertical sectional view of another modified form of the device of this invention, wherein a transverse shelf is illustrated in the water seal, for enhancing visual observation of bubbles passing through the seal.

With reference to FIG. 16 there is illustrated another alternative embodiment of a device 400, in accordance with the present invention. In FIG. 15, the device 400 is constructed preferably generally similar to the other embodiments described herein, except that at the lower end of the separation wall 402 between conduits 403 and 404 of the water seal chamber, there is provided a laterally extending shelf 405, the lower surface of which is tapered at "a", to preferably be within an angular range of 2-5 degrees. This provides a mechanism whereby air bubbles traveling in the direction of arrow 406, down through conduit 403, through the chamber 401, may roll along the bottom surface of the shelf 405, as illustrated in FIG. 16, giving them a longer period of residence as they traverse the separator 402, which tends to magnify the opportunities to observe the rate of air flow through the water sealed chamber. In instances where there is an air leak between the lung and the pleural cavity (pleurothax) of the patient or the like that is being evacuated of liquid, such visual observation provided to an attendant permits early diagnosis of the air leak and monitoring of healing and closure of the same.

Figure 17:
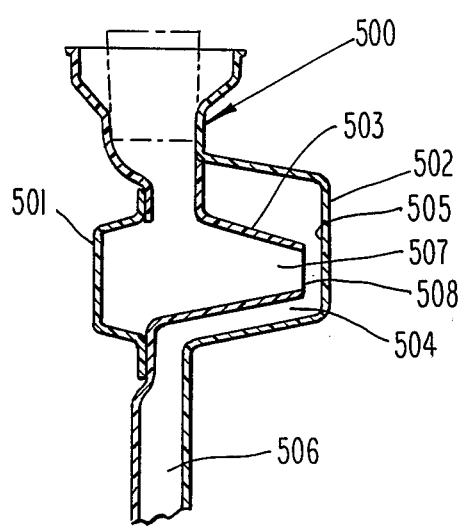
FIG. 17 is a fragmentary vertical sectional view of the upper portion of a modified device of this invention to that illustrated in FIG. 9, but wherein a baffle is provided as an alternative fluid control for preventing liquid flow while permitting air flow.

With particular reference to FIG. 17, there is illustrated another form of fluid control means for preventing undesired communication of liquid from one chamber to another, or outwardly of the apparatus, for example upon tipping of the device 500 onto a front face 501 or back face 502, if the device 500 is upset either leftwardly or rightwardly as viewed in FIG. 17, off its base (not shown). In the arrangement of FIG. 17, there is provided a baffle 503, in the form of a slightly downwardly sloped frusto-conical protrusion, or funnel-like member 503, extending into a surrounding liquid reception zone 504, but stopping short of a wall 505 thereof. Thus, if the device 500 is tipped rightwardly, as by falling clockwise as viewed in FIG. 17, liquid from below the conduit 506 may enter the reception zone 504, and enter the interior 507 of the baffle through its inlet 508. However, the capacity of the reception zone 504 and the lateral protrusion of the baffle 503 as viewed in FIG. 17 will be constructed to have a predetermined size relative to the amount of liquid that will normally be contained below conduit 506, such that the amount of liquid that could fall onto the zone 504 will never be an amount sufficient to rise to the top of the tapered baffle 503 in its clockwise-fallen position. Similarly, if the device 500 were to tip in a counterclockwise direction, on to its face 501 relative to its disposition in FIG. 17, liquid from below conduit 506 could not rise in liquid reception zone 504 sufficiently high to enter the opening 508 of the baffle 503. Thus, the device functions as a fluid control means alternative to the gas permeable, liquid impermeable filter membrane discussed above. It will be noted that the illustration of FIG. 17 is representative only, in order to avoid duplication hereof, and that the baffle 503 may, if desired, be substituted for each instance where such a filter membrane has been discussed hereinabove, although without the safe pressure management provided by the filters.

Figure 18:
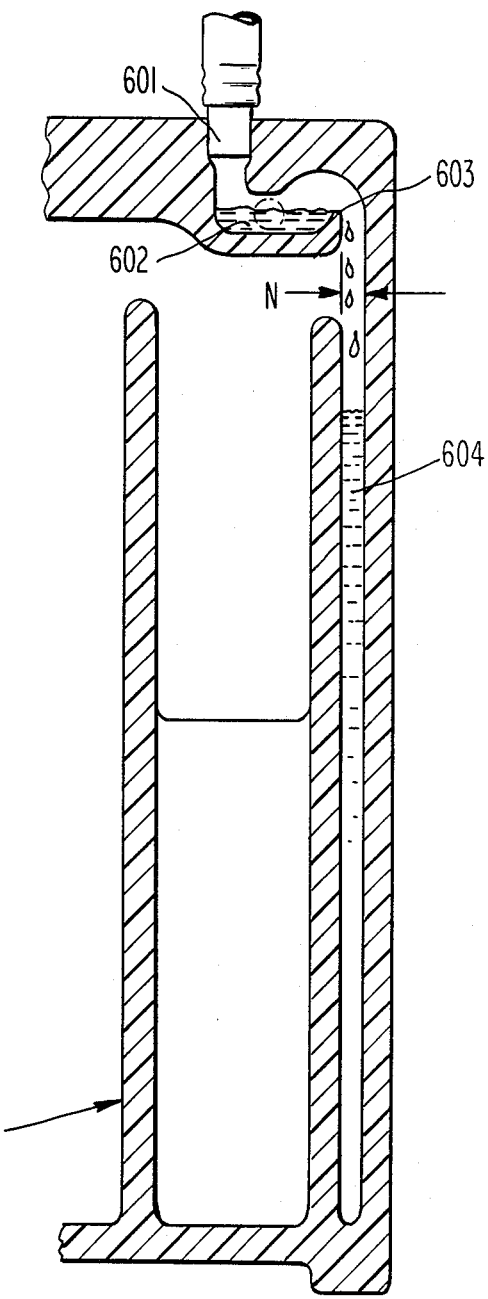
FIG. 18 is a fragmentary vertical sectional view, similar to that illustrated at the right end of FIG. 2, but wherein an additional chamber section is illustrated at the right end of the device.

With reference now to FIG. 18, there is illustrated another alternative embodiment of the device of this invention, generally designated by the numeral 600, which, while being fragmentally illustrated, is constructed similar to the other embodiments discussed herein, but wherein the liquid inlet opening 601 is adapted to receive liquid into a trough 602, and the trough has its dam 603 so located that liquid flow over the dam will fall into a very narrowly configured chamber section 604, to permit the greatest possible rise in height of a given amount of liquid for increased visual observation of color, particle accumulation, liquid separation, and numerous other factors that may be of interest to the attendant. As discussed above, a removable tape, calibrated with indicia, and capable of being written thereon, may be provided on the outside or casing of the device, for measuring and recording the observations within the chamber section 604. It will also be noted that the location of the dam 603 is in close relationship to and preferably slightly laterally extending to an amount less than the narrow width "N" of the chamber section 604 as indicated.

Figure 19:
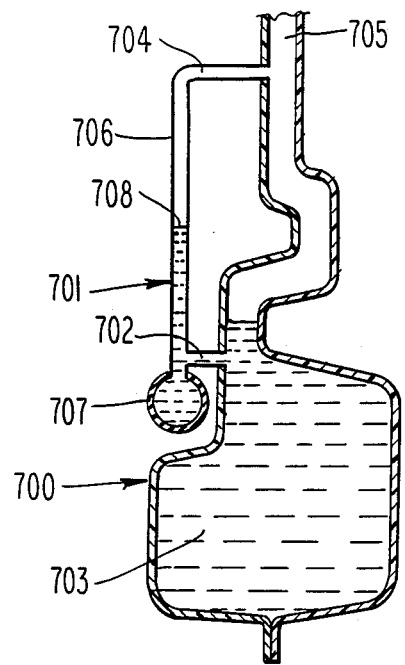
FIG. 19 is an illustration of another alternative visual indicator for observation of an air leak, in the form of a bubble flowmeter.
Figure 20:
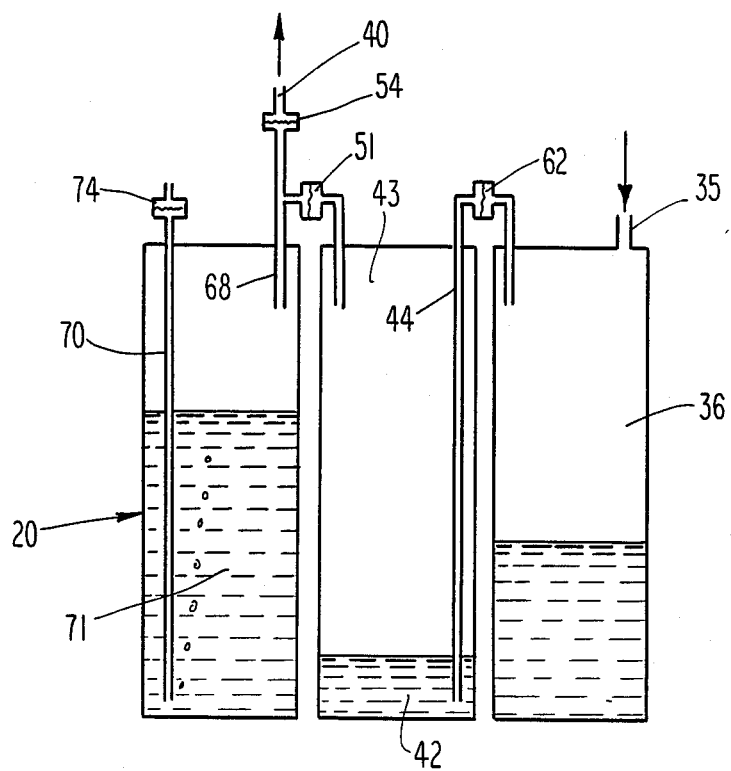
FIG. 20 is a schematic representation of an embodiment of the apparatus of this invention in the format of a three bottle system.

In FIG. 19, an alternative device 700 to the shelf 405 of FIG. 16 for greater visual observation of an air leak is illustrated in the form of a bubble flowmeter 701, having an inlet 702 from the below-water level of the water seal chamber 703, and an outlet 704 to the vacuum draw outlet leg 705, with a vertical observation duct 706 therebetween, whereby a small amount of a detergent or other emulsifying agent is added to water in the seal chamber 703 and a preferably rubber squeeze bulb 707 is squeezed and allowed to expand, withdrawing soapy water into the bulb 707 and into duct 706. Therefore as a bubble of air evidencing a leak, such as between a lung and pleural cavity, enters duct 706 through inlet 702, it will form a readily observable meniscus 708, and travel up the duct 706 at an observable rate which may be recorded as volume versus measured time based on indicia or a scale (not shown) on the exterior of duct 706, thereby providing a valuable diagnostic tool. While bubble meters per se are known to exist, their application to a drainage apparatus of the present type is believed to be novel.

It will thus be apparent that the present invention is highly advantageous in that it provides a unit that can be safer, one that can be used after being upset, one which affords superior diagnostic capabilities, one which can be constructed to be sufficiently short in height to fit under a bed or the like to avoid opportunities for being upset, one which is easier to fill, and one which can be carried around by an ambulatory person. It will further be noted that the device can be pre-filled if desired, and provided with a precise amount of water in the pertinent cavities thereof. In many instances, it will be preferable to provide the device with pre-packaged containers of water, premeasured in amount, with one container being provided for the water seal chamber and another, larger container being provided for the manometer. With the use of superior drainage equipment such as this, in medical situations, costs can be reduced by enabling patients to be removed from more complicated diagnostic equipment at an earlier time, enabling earlier discharge of the patient from the hospital.

Various modifications can be made in the details of construction, the use and operation of the device, all within the spirit and scope of the invention as defined in the appended claims.

What is claimed is:

1. A drainage apparatus for collection of matter including liquids and any solids carried therewith from a body cavity of a mammal when in normal, upstanding disposition, said apparatus comprising:
   (a) a vacuum opening,
   (b) a collection chamber having an inlet opening adapted to be placed in communication with the cavity to be drained, with said chamber being in fluid communication with the vacuum opening,
   (c) a sampling collection means in the apparatus at the inlet opening to the collection chamber for accumulating a specimen of recent inlet matter therein, and an openable access means to the sampling collection means from outside the apparatus for sampling a specimen from the collection means,
   (d) a means vacuum line for regulating the vacuum drawn on the collection chamber, and
   (e) a gas permeable, liquid impermeable one way valve means for allowing gas flow between said collection chamber and the vacuum opening only from the collection chamber to the vacuum opening when the apparatus is in said normal, upstanding disposition, and said valve means being constructed so as to act as a seal when the chamber is upset.

2. A drainage apparatus for collection of matter including liquids and any solids carried therewith from a body cavity of a mammal, said apparatus comprising:
   (a) a vacuum opening,
   (b) a collection chamber having an inlet opening adapted to be placed in communication with the cavity to be drained, with said chamber being in communication with the vacuum opening,
   (c) a liquid seal chamber means having first and second conduits for receiving liquid therein in liquid sealing relationship between the first and second conduits; with said first conduit being in fluid communication with said collection chamber, and
   (d) fluid control means disposed across at least said first conduit for preventing liquid flow thereacross while permitting gas flow thereacross.

3. A drainage apparatus for collection of matter including liquids and any solids carried therewith from a body cavity of a mammal, said apparatus comprising:
   (a) a vacuum opening,
   (b) an atmosphere opening,
   (c) a collection chamber having an inlet opening adapted to be placed in communication with the cavity to be drained, with said chamber being in fluid communication with said vacuum opening,
   (d) a manometer having a water chamber and conduits on opposite sides thereof, in fluid communication with each other through said water chamber, and and
   (e) fluid control means disposed across at least one said conduit for preventing liquid flow thereacross while permitting gas flow thereacross.

4. The apparatus of claim 3, including a liquid seal chamber having first and second conduits wherein said manometer conduits are third and fourth conduits and with said third conduit being in fluid communication with said second conduit of said liquid seal chamber and with the vacuum opening; and with said fourth conduit being in fluid communication with the atmosphere opening.

5. The apparatus of any one of claims 2-4, wherein said fluid control means comprises baffle means.

6. The apparatus of any one of claims 2-4, wherein said fluid control means comprises a gas permeable, liquid impermeable member.

7. The apparatus of any of claim 6 and wherein said member comprises a membrane sheet of material.

8. The apparatus of claim 6, wherein said fluid control means comprises a gas permeable, liquid impermeable member disposed in a vertical plane, in the normal upstanding disposition of the device.

9. The apparatus of claim 4, wherein said fluid control means is disposed between said atmosphere opening and the manometer fourth conduit.

10. The apparatus of claim 4, wherein said fluid control means is disposed between the first conduit and the collection chamber.

11. The apparatus of claim 4, wherein said fluid control means is disposed between the manometer third conduit and said vacuum opening.

12. The apparatus of claim 4, wherein said fluid control means is disposed between the manometer third conduit and the seal chamber second conduit.

13. The apparatus of any of claims 2 and 4, wherein said fluid control means is disposed between the seal chamber second conduit and said vacuum opening.

14. A drainage apparatus for collection of matter including liquids and any solids carried therewith from a body cavity of a mammal, said apparatus comprising:
（a) a vacuum opening,
(b) a collection chamber in fluid communication with said vacuum opening and having an inlet opening adapted to be placed in communication with the cavity to be drained,
(c) a removable and repositionable supporting base adapted for mechanical engagement at the lower end of the device, with the device having front and rear walls in an upstanding position of use thereof, with the base having legs extending in opposite directions, with said legs extending substantially beyond said walls in one position of the base on the device and having no substantial extension of the legs beyond said walls in another position of the base on the device, and
(d) wherein said base is provided with four upstanding wall-engaging friction-fit fingers with each said finger having a plurality of chamber engaging surface means providing two alternate engagement surfaces.

15. A drainage apparatus for collection of matter including liquids and any solids carried therewith from a body cavity of a mammal, said apparatus comprising:
(a) a vacuum opening,
(b) an atmosphere opening,
(c) a collection chamber having an inlet opening adapted to be placed in communication with the cavity to be drained,
(d) a liquid seal chamber having first and second conduits and adapted to receive liquid therein in liquid sealing relationship between the first and second conduits; with said first conduit being in fluid communication with said collection chamber
(e) a manometer having a water chamber and third and fourth conduits and adapted to receive liquid in its chamber between the third and fourth conduits; with the third conduit being in fluid communication with the second conduit of the liquid seal chamber and with the vacuum opening; and with the fourth conduit being in fluid communication with the atmosphere opening, and
(f) said apparatus being defined by upstanding walls and upper and lower end walls in upstanding orientation of the device in normal use; with said atmosphere opening having entries thereto lying in a plurality of nonparallel planes.

16. The apparatus of any one of claims 1, 2-4, including at least one openable access port to a liquid receiving collection zone from outside the device for sampling a specimen therethrough.

17. The apparatus of claim 16, wherein said port is provided with a sampling valve normally closed but openable for sampling access.

18. The apparatus of claim 17, wherein said valve is of the needleless type, characterized in that said valve contains tool receiving means whereby insertion of a tool means opens said valve for sampling access.

19. The apparatus of claim 2, including at least one openable access port to a liquid receiving collection zone from outside the device for sampling a specimen therethrough, and wherein said collection zone comprises the liquid seal chamber.

20. The apparatus of claim 3, including at least one openable access port to a liquid receiving collection zone from outside the device for sampling a specimen therethrough, and wherein said collection zone comprises the manometer water chamber.

21. A drainage apparatus for collection of matter including liquids and any solids carried therewith from a body cavity of a mammal, said apparatus comprising:
(a) a vacuum opening and a liquid seal chamber having first and second conduits,
(b) an atmosphere opening,
(c) a collection chamber having an inlet opening adapted to be placed in communication with the cavity to be drained,
(d) a manometer having a water chamber means and third and fourth conduits to receive liquid in its chamber means between the third and fourth conduits; with the third conduit being in fluid communication with the second conduit of said liquid seal chamber and with the vacuum opening; and with the fourth conduit being in fluid communication with the atmosphere opening, and
(e) said manometer being generally U-shaped with the third and fourth conduits comprising at least portions of different legs of the U-shape with the water chamber means therebetween for bubbling of air from atmosphere therethrough upon application of a vacuum to the third conduit; including a bubble breaker disposed in the water chamber and located a sufficient distance above the bottom of the chamber to allow bubbles passing through the chamber to achieve sufficient velocity to break upon striking the bubble breaker.

22. The apparatus of claim 21, wherein the bubble breaker comprises a reticulated foam insert across said chamber.

23. A drainage apparatus for collection of matter including liquids and any solids carried therewith from a body cavity of a mammal, said apparatus comprising:
(a) a vacuum opening,
(b) a collection chamber in fluid communication with said vacuum opening,
(c) said collection chamber having an inlet opening adapted to be placed in communication with the cavity to be drained,
(d) a liquid seal chamber having first and second conduits and adapted to receive liquid therein in liquid sealing relationship between the first and second conduits; with said first conduit being in fluid communication with said collection chamber, and
(e) said liquid seal chamber and first and second conduits together comprising a generally U-shaped configuration for bubbling of air through the seal from the first conduit to the second conduit upon application of a vacuum to the second conduit; including air bubble observation enhancement means at the bottom of said U-shaped configuration for permitting air bubble flow therealong from the first conduit to the second conduit upon application of a vacuum to the second conduit, for facilitating the observation of air bubbles passing therealong, and wherein the enhancement means comprises a laterally extending upwardly-angled shelf.

24. A drainage apparatus for collection of matter including liquids and any solids carried therewith from a body cavity of a mammal, said apparatus comprising:
(a) a vacuum opening, (b) a collection chamber in fluid communication with said vacuum opening, and having an inlet opening adapted to be placed in communication with the cavity to be drained, (c) a second collection chamber having its own inlet opening adapted to be placed into communication with a second cavity to be drained, with vacuum communication means between said collection chambers at upper ends thereof, for simultaneous collection of matter from two cavities with one vacuum source, and (d) a fluid control means in said vacuum communication means between said chambers, for preventing liquid flow therethrough while permitting gas flow therethrough.

25. The apparatus of claim 24, wherein said fluid control means comprises a gas permeable, liquid impermeable member.

26. The apparatus of any one of claims 2, 3 and 4, wherein said chambers are substantially constructed each as front and back portions of a two part molded structure with front and back portions joined along a common plane; with said fluid control means comprising a gas permeable, liquid impermeable member being disposed in said common plane.

27. A drainage apparatus for collection of matter including liquids and any solids carried therewith from a body cavity of a mammal, said apparatus being normally disposed in upstanding relation and comprising:
(a) a vacuum opening,
(b) a collection chamber having an inlet opening adapted to be placed in communication with the cavity to be drained,
(c) a liquid seal chamber having first and second conduits generally vertically disposed conduits in the upstanding disposition of the apparatus, and adapted to receive liquid therein in liquid sealing relationship between the first and second conduits; with said first conduit being in fluid communication with said collection chamber, including trapping means comprising a laterally disposed part of said seal chamber for trapping air therein upon lateral upsetting the apparatus at about a right angle to its normal upstanding disposition
(d) said apparatus having a top wall, said walls and a bottom wall which when in a upstanding position said bottom wall of said apparatus forms the bottom wall of said seal chamber, said seal chamber conduits extending upwardly from said seal chamber.

28. The apparatus of claim 27, with a fill opening at an upper portion of one of the conduits and having a closure thereat, said closure being free of substantial protrusion beyond the rest of the apparatus.

29. The apparatus of claim 27, with a fill opening at an upper portion of one of the conduits and having a closure thereat, including bacteria filter means across said fill opening for filtering bacteria from water being applied into the opening.

30. The apparatus of any one of claims 2–4, with said apparatus being adapted for upstanding disposition during use, with liquids in chambers at lower ends of the apparatus, and visual indicating means at an upper end of said apparatus for retaining an amount of liquid delivered thereto upon the apparatus being upset from its normal upstanding position, after return of the apparatus of its normal upstanding disposition.

31. The apparatus of claim 27, including opening means for filling the liquid seal chamber in a generally horizontally disposed side thereof when the apparatus is in a right-angle-upset disposition.

32. The apparatus of claim 31, wherein said visual indicating means comprises a receptacle portion for receiving and retaining liquid.

33. The apparatus of claim 15, with a removable and repositionable supporting base adapted for frictional engagement at the lower end of the apparatus, with the apparatus having front and rear walls in an upstanding position of use thereof, with the base having legs extending in opposite directions, with said legs extending substantially beyond said walls in one position of the base on the apparatus and having no substantial extension of the legs beyond said walls in another position of the base on the apparatus, said apparatus being defined by upstanding walls and upper and lower end walls in upstanding orientation of the apparatus in normal use, at least one openable access port to a liquid receiving collection zone from outside the apparatus for sampling a specimen therethrough, wherein said openable access port is provided with a sampling valve, a removable tape having means for securing it for application to an outer surface of said collection chamber, said tape having numerical indicia thereon for indicating liquid quantity within said chamber at any given time; and tape being capable of being written thereon, with the tape being of a type permitting removal and attachment to some other surface, said manometer being generally U-shaped with the third and fourth conduits comprising at least portions of different legs of the U-shape with the water chamber therebetween for bubbling of air from atmosphere therethrough upon application of a vacuum to the third conduit; said collection chamber comprising a plurality of chamber sections, each separated by a generally vertical separation wall, with each said separation wall being of a different height, and with the separation wall closest to said inlet opening being of the shortest height, wherein the liquid seal chamber and first and second conduits together are substantially U-shaped with the chamber between the conduits, wherein the manometer chamber and third and fourth conduits together are substantially U-shaped with the chamber between the conduits, with said apparatus being adapted for upstanding disposition during use, with liquids in chambers at lower ends of the device, and visual indicating means at an upper end of said apparatus for retaining an amount of liquid delivered thereto upon the apparatus being upset from it normal upstanding disposition after return of the apparatus to its normal upstanding disposition, including a sampling trough at the inlet to the collection chamber, and with fluid control means of the gas permeable, liquid impermeable sheet type means disposed across at least one said conduit for preventing liquid flow thereacross while permitting gas flow thereacross.

34. The apparatus of claim 27 including sizing of chambers such that ratio of water filled volume to air filled volume of seal and manometer chambers, such that the fluid control means are covered with fluid on an upset to at least horizontal, thus shotting off vacuum and also preventing reflux of air and/or fluids to patient.

35. A drainage apparatus for collection of matter including liquids and any solids carried therewith from a body cavity of a mammal, said apparatus comprising:
(a) a vacuum opening, (b) a collection chamber in fluid communication with said vacuum opening.
(c) said collection chamber having an inlet opening adapted to be placed in communication with the cavity to be drained,
(d) a liquid seal chamber having first and second conduits and adapted to receive liquid therein in liquid sealing relationship between the first and second conduits; with said first conduit being in fluid communication with said collection chamber,
(e) said liquid seal chamber and first and second conduits together comprising a generally U-shaped configuration for bubbling of air through the seal from the first conduit to the second conduit upon application of a vacuum to the second conduit; including air bubble observation enhancement at the bottom of said U-shaped configuration for permitting air bubble flow therealong from the first conduit to the second conduit upon application of a vacuum to the second conduit, for facilitating the observation of air bubbles passing therealong; and wherein the enhancement means comprises a bubble flow meter device in fluid communication with the interior of the liquid seal chamber; characterized in that said bubble flow meter comprises a duct means paralleling said liquid seal chamber with inlet and outlet means to said liquid seal chamber; a mixing means depending from said duct; and an emulsifying means contained within said duct.

* * * * *

UNITED STATES PATENT OFFICE
CERTIFICATE OF CORRECTION

Patent No. 4,767,417              Dated August 30, 1988

Inventor(s)   John R. Boehringer, et al.

It is certified that error appears in the above-identified patent and that said Letters Patent are hereby corrected as shown below:

35 U.S.C. 254

Column 2, line 6, "Ir" should be "It".
Column 2, line 21, "he" should be "the".
Column 11, line 63, "means vacuum" should be "vacuum means" and the word "line" should be deleted.
Column 12, line 34, the second "and" should be deleted.

Signed and Sealed this

Fourteenth Day of February, 1989

Attest:

DONALD J. QUIGG

Attesting Officer     Commissioner of Patents and Trademarks